United States Patent
Stangel et al.

(10) Patent No.: US 6,444,724 B1
(45) Date of Patent: Sep. 3, 2002

(54) COMPOSITE MATERIALS AND ADHESION PROMOTERS FOR DENTAL APPLICATIONS

(75) Inventors: Ivan Stangel, Bethesda, MD (US); Thomas Ellis, Hudson (CA); Erik Kruus, Saint-Hubert (CA); Edward Sacher, Montreal (CA); Robin Drew, Pt. Claire (CA); Jingwei Xu, Montreal (CA)

(73) Assignee: BioMat Sciences, Inc., Rockville, MD (US)

( * ) Notice: Subject to any disclaimer, the term of this patent is extended or adjusted under 35 U.S.C. 154(b) by 0 days.

(21) Appl. No.: 09/467,173

(22) Filed: Dec. 20, 1999

Related U.S. Application Data

(63) Continuation of application No. PCT/US98/12715, filed on Jun. 18, 1998.
(60) Provisional application No. 60/050,973, filed on Jun. 19, 1997.

(51) Int. Cl.[7] .............................. A61K 6/04; C08K 3/10; C08K 5/37
(52) U.S. Cl. ........................ 523/116; 523/115; 523/205; 523/209; 524/392; 524/440; 524/395; 524/547; 526/286; 526/289
(58) Field of Search ................................. 523/115, 116, 523/205, 209; 524/392, 395, 440, 547; 526/286, 289

(56) References Cited

U.S. PATENT DOCUMENTS

| | | | | |
|---|---|---|---|---|
| 4,713,403 A | * | 12/1987 | Yoshida et al. | 523/116 |
| 4,816,495 A | * | 3/1989 | Blackwell et al. | 523/116 |
| 5,064,495 A | | 11/1991 | Omura et al. | 433/217.1 |

* cited by examiner

Primary Examiner—Peter Szekely
(74) Attorney, Agent, or Firm—Fitch, Even, Tabin & Flannery

(57) ABSTRACT

Composite materials particularly suitable in the dental art as a tooth filling material including a polymer matrix, a metal, metal alloy, metal oxide particulate, or combinations thereof, in the presence or absence of colloidal silica, and a coupling agent to adhere the particulate to the polymer matrix. Adhesion can also be facilitated by cleaning and/or coating the particulates prior to incorporation into the polymer matrix. One or two paste systems of the composition with suitable initiators, accelerators, etc. can be formulated.

19 Claims, 5 Drawing Sheets

COMPOSITE MATERIALS AND ADHESION PROMOTERS FOR DENTAL APPLICATIONS

This application is a continuation of PCT/US98/12715 filed Jun. 18, 1998 which claims the benefit of provisional application Ser. No. 60/050,973, filed Jun. 19, 1997.

BACKGROUND OF THE INVENTION

1. Field of the Invention

The invention relates to curable composite materials and adhesion promoters for biomedical applications, especially dental applications.

2. Description of the Related Art

Composite materials are used for a variety of applications in the biomedical field. Objects being composed of such materials, in part or in whole, can be classified as medical devices. In the dental field, composite materials are used to restore teeth to form and function, in part, or in whole.

Dental amalgam, commonly used as a filling material for teeth, is made from a powdered alloy and mercury. The alloy primarily contains silver, tin, and copper. Other metals are present at concentrations that are relatively low compared to silver, tin or copper. The alloy is mixed with mercury to produce dental amalgam. The wetting of metal alloy particles by mercury produces a plastic mass that can easily be inserted into a cavity preparation and shaped, after which time it hardens. Mercury is used for dental amalgam as it is the only metal that exists in a liquid state at room temperature. It is thus capable of wetting the alloy powder, a process which initiates hardening. The presence of mercury in dental amalgam is controversial, as numerous studies have demonstrated that mercury is released during in-service use. This release has generated much interest in developing new, safe and functional alternatives to dental amalgam.

A class of materials known as composite resins are commonly used as alternatives to dental amalgam. Composite resins generally contain a polymer phase (a matrix) reinforced by inert fillers, these generally consisting of various forms of amorphous silica ($SiO_2$), or polymorphs of silica. The fillers are bound to the matrix via silane couplers, with γ-methacryloxypropyl trimethoxysilane (γ-MPS) being the most commonly used silane. Siloxane linkages are formed to the filler on the silicon end of the coupler. The methacrylate moiety at the other end of the coupler co-polymerizes with the matrix. Modern composites additionally contain photoinitiators, accelerators, colorants and additives for maintaining chemical stability.

The longevity of different materials in dental restorations is important in assessing their effectiveness. Several cross-sectional studies have shown that the median age for composite restorations is 5 to 8 years, while that for amalgam restorations is 8 to 14 years. In a prospective study of up to five years duration, failure rates for composite restorations were approximately twice that of amalgam restorations. These survival relationships were similarly observed in children, where the median survival time for amalgam restorations was 5 years while that for composite restorations was 32 months. These data would clearly suggest that metal-based restorations are superior to conventional composite resins with respect to survival.

Confirmation of the superiority of metal-based direct restoratives can be additionally gleaned from two initiatives in developing alternatives to amalgam that involve the use of silver. One alternative is a pure silver powder which is cold-welded into a solid mass by hand pressure. The other alternative involves mixing a silver alloy with gallium, a metal in liquid phase at near-room temperature. The silver powder project appears to have some promise; however, the technique of placement may be time consuming, and could limit the widespread utility of the material. The gallium-containing alloy has been shown to be sensitive to water at its early stage of set, and requires coating with a varnish to avoid water contact for the first 24 hours.

SUMMARY OF THE INVENTION

The invention features a composition, which, when hardened, is suitable for application in the biomedical arts, such as in dentistry where it can be used as a filling or restorative material for teeth.

The invention also features a composition including a filler of metal, or a metal alloy, or a metal oxide, or a structure or structures having a metal coating, or combinations thereof, with or without surface modification. These surface modifications include methods to remove surface impurities, such as oxide layers or organic impurities. Surface modifications can also include the deposition of metal films on the surfaces of the fillers. The composition has excellent physical and mechanical properties on hardening.

The invention also features polymerizable compositions that contain fillers, the surface of these fillers having the ability to form bonds to the sulfur of a thiol. The thiol contains a moiety that is capable of bonding to a polymerizable component of the composition.

The invention also features new coupling agents, which form bonds between the surface of the filler structure and the polymerizable component of the composition.

The invention also features a method of preparing adhesion promoters having thiol functionalities which, on one end, form bonds with the surface of the filler structures and on the other end, are capable of reacting with a polymerizable component of the composite composition.

The invention also features a method of preparing adhesion promoters having phosphate functionalities which, on one end, are reacted with the surface of the filler structures, and on the other, are capable of reacting with a polymerizable component of the composite composition.

This invention features a composition of a composite material including a polymerizable material constituting a matrix, a filler, a coupling agent, stabilizers and an initiator system. The matrix is a binder into which particles of regular or irregular shape can be embedded, these particles being the filler. A coupling agent is a chemical structure that includes functionalities capable of reacting with different substances, the purpose of the coupling agent being to bond dissimilar materials to each other. In the composition featured, one of the functionalities is capable of polymerizing with the polymerizable matrix. Stabilizers are compounds that prevent the premature polymerization of the polymerizable material in the composition. Initiator systems include agents that initiate polymerization when subjected to an activating source. The composite can be used as a filling material in teeth, or as a material to re-establish the structure of teeth, in part or in whole, although it can be used in other applications requiring high-strength composites.

The matrix contains a material or materials having polymerizable moieties. The filler can include metal, metal alloy, or metal-oxide particles. The filler particles can be surface modified. The filler can also include any particles having surfaces that can react with the sulfur of a thiol. The filler can be dispersed in the matrix. The polymerization of the composite material can be activated by chemical methods, by heat, or by irradiation, such as a laser, or other visible or ultraviolet light source, or by microwave energy. Depending on the method of curing, the composition can be provided as a one-paste system, or it can be divided into two pastes. In the latter case, the composite hardening is chemically activated. One paste of the two-paste system contains the composite material and chemical initiator while the second paste contains the composite material and the chemical activator, which can be an amine accelerator. Single paste systems contain both an initiator and an amine accelerator in the single paste.

Surface modifications include the removal of surface impurities using various cleaning procedures, such as the treatment of the particles with acids. Surface modification also can involve the deposition of a thin silver or gold film on alloy particles. The coupling agent can be a form of a silane, but preferably, are thiol or phosphate compounds that bond metal or metal alloy particulates, or particulates consisting of oxides of metals to the polymerizable matrix. A metal oxide filler can be bonded to the matrix via a silane coupling agent.

The invention particularly features a metal, or a metal-alloy particle, or metal-oxide particle, or other ceramic particles, or any particle whose surface can form bonds with sulfur, these particles being used alone, or in combination, which are especially of interest as a filler in composites.

This invention also features a method of forming bonds between the sulfur of a thiol and the filler of the composite material. The thiol compounds have functionalities which can react with the polymerizable matrix of the composite material. The thiol can be deposited on the surface of a filler to form metal-sulfur bonds.

This invention also features a method of constructing and depositing a phosphate compound on metal, metal alloy or metal oxide particles, the phosphate compound having the capability of reacting with the polymerizable matrix of the composite material.

The compounds and methods of the invention can be used to bond particles having surfaces capable of forming bonds to the sulfur of a thiol to polymerizable components of any polymerizable material. The method includes coupling thiol compounds to a material, the thiol including a polymerizable component. Examples of this use include glass ionomer materials that have been modified to contain unsaturated groups capable of being polymerized.

Composite materials that harden when placed directly in the tooth would have improved strength using fillers such as metal, or metal alloy, or metal oxide particles. Composite materials having fillers bonded to the matrix using coupling agents containing a thiol or a phosphate moiety would have improved durability in a water environment by being more resistant to hydrolysis than silane coupled fillers.

This invention finds utility in formulating new composites containing metal, metal alloy, or metal-oxide fillers, or a combination thereof, dispersed in a matrix phase. Preferably, the surface of the filler can form a bond with the sulfur of a thiol. If the surface of the filler cannot form such a bond, then a film of a metal that can form a bond with the sulfur of a thiol can be deposited on the filler. The fillers are coupled to the composite matrix using new adhesion promoters based on alkylthiols. Coupling agents containing a phosphate functionality can be used to bond the fillers to the matrix in cases where a sulfur bond to the surface of the filler cannot be formed.

Thiols form chemical bonds to metal surfaces by the interaction of sulfur with metal (S-metal bonds). The formula for a thiol is given by:

HS-R where R is an alkyl or substituted alkyl having from 2 to 100 carbon atoms, preferably 4 to 40 carbon atoms, and more preferably 6–20 carbon atoms. The substituent can be a terminal polar group having a specific functionality for reaction with other compounds. For example, the terminal group can be an acrylate. The number of carbon atoms and the nature of the substituent can be controlled to change the properties of the R group.

Thiols are capable of coupling metals to polymers. For example, a pendant thiol can be used to couple steel surfaces to a polymer matrix. Additionally, glycolic thioesters can form an S-metal bond, leaving chains that promote the adhesion of acrylate and epoxy adhesives. In addition to binding to the surface, a thiol group is also capable of an addition reaction across a vinyl group. Thiol-ene polymerizations such as, for example, a two component coupling-agent layer used to bond copper with epoxy and polyimide resins is more resistant to corrosion, and can provide higher adhesive strength than either component alone, even at high temperatures.

With respect to phosphates, the surface treatment of metal by phosphate is well-known as phosphating. A solution containing the free phosphoric acid, a primary metallic phosphate, and an accelerator are used in phosphating procedures. The surface physical or physico-chemical properties of metal surfaces, such as aluminum and its alloys, are modified by this procedure. Phosphate compounds can be deposited on the surface of metal or metal oxides by phosphating procedures.

Additional features and advantages of the invention will become apparent from the detailed description of the invention.

DETAILED DESCRIPTION OF THE PREFERRED EMBODIMENTS

Figure 1:
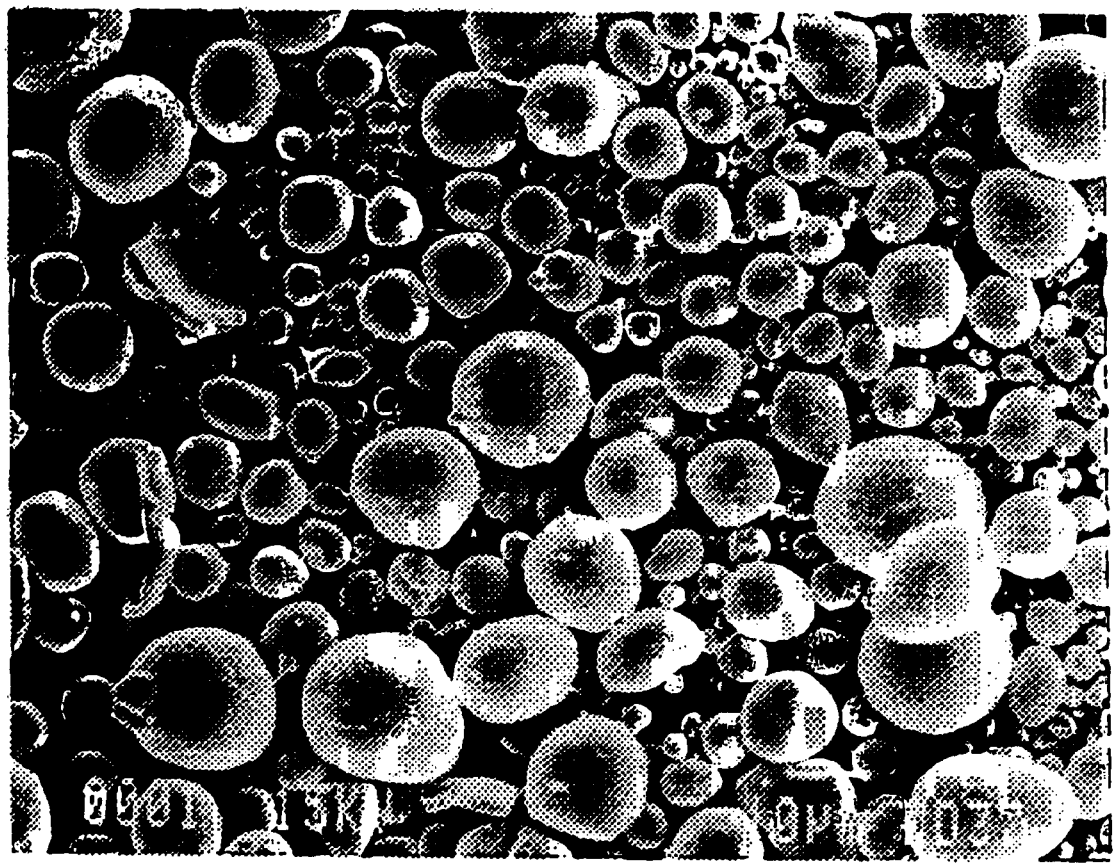
FIG. 1 is a scanning electron micrograph of particles of silver alloy.

Briefly, the preferred invention provides a composition, which consists of a resin matrix, a filler, a coupling agent and an initiator system. The composition is particularly suitable as a filling material for teeth, having a preferable use in load-bearing surfaces of teeth. The composite has superior performance by use of metal, or metal alloy, or metal oxide particles, or a combination of the preceding, with or without surface modification, as a filler, or as fillers dispersed in a polymer, in combination with different types of coupling agents. Surface modifications include the removal of surface impurities, such as oxides or hydrocarbons, or hydrocarbon containing compounds, using various cleaning procedures, such as the treatment of the particles with acids. Surface modification can also involve the deposition of a thin film of a noble metal, such as silver, gold, platinum, or palladium on filler particles. This deposition can promote the formation of sulfur bonds to the surface of the filler particles. Other metals may be used for forming the film on the filler particles, the key factor in the selection of the metal to be used for forming the film being that it is able to form a bond with sulfur. If a film is formed on the filler particles to be used in the composition, then cleaning procedures can be used to remove impurities on the surface.

The adhesion promoters are preferably polymerizable thiol-containing compounds that act as coupling agents between the filler particles and a polymerizable material in the composition. If a sulfur bond cannot be formed to the surface of filler particles to be used in the composition, such as in the case where an oxide layer prevents the formation of such bonds, coupling agents can be a form of a polymerizable phosphate compound or a silane.

For curing by irradiation, such as by exposure to a laser, or other visible light or ultra-violet light source, or by microwave, the composition can be provided in a single paste system, and contains sensitizers with reducers to harden the paste. For chemical initiation, the composition can be divided into two pastes, with one paste containing the composite and initiators while the second paste contains the composite and accelerators. The curing or hardening will be carried out by mixing the two pastes together, or by heating or UV light depending on the initiator and accelerator used in these two pastes.

In accordance with the present invention, the composition includes a polymerizable material used as a matrix, stabilizers, and an indicator. The filler includes particles having surfaces which can form bonds with sulfur, phosphorus or silicon.

The composition comprises a polymerizable material in an amount of from about 1 to about 79 percent by weight of the composition, a filler in an amount of from about 20 to about 98 percent by weight of the composition having a coating of a metal selected from groups VIIB, VIII, IB, IIB and IVA of the Periodic Table of the Elements or their oxides; and a coupling agent which includes a functionability capable of bonding with the metal. At least 0.01 percent weight coupling agent can be used.

The polymerizable material includes an acrylate monomer, a methacylate monomer, a phosphate of an acrylate monomer or a phosphate of a methacrylate monomer.

The polymerizable material used as a matrix is formed from monomers of acrylates or methacrylates having at least one unsaturated carbon-carbon double done in an amount ranging from 0.01 to 50 weight percent of the total composition, more preferably 0.1 to 30 weight percent, and most preferably 1 to 20 weight percent of the total composition. Suitable monomers include 2,2-bis[4-(2-hydroxy-3-methacrylyloxypropoxy)phenyl]propane (BisGMA), ethyleneglycol dimethacrylate (EGDMA) and triethyleneglycol dimethacrylate (TEGDMA), 1,6-hexamethylene glycol dimethacrylate (HGDMA), trimethylolpropane trimethyacrylate (TMP-TMA), pentaerythritol triacrylate, pentaerythritol tetraacrylate, urethane dimethacrylatne, 2-hydroxyethyl methacrylate, or 2-hydroxymethylmethacrylate. The polymerizable material can also be formed from monomers such as pentaerythritol triallyl ether, eutectic monomers, hydrophobic monomers, or spiro orthocarbonates.

The filler includes metal, or metal alloy, or metal oxide particles. The metal can be a noble metal, such as silver, gold, platinum, palladium, rhodium, ruthenium, iridium or osmium. The metal can also be indium, titanium, vanadium, chromium, manganese, iron, cobalt, nickel, copper, zinc, tin, zirconium, or aluminum. The metal alloy can be an alloy containing silver, gold, platinum, palladium, zinc, or copper. A silver alloy, for example, can contain silver in the range of 40–85 weight percent, preferably in the range of 45–70 weight percent, and most preferably in the range of 50–65 weight percent; tin in the range of 25–35 weight percent, most preferably in the range of 27–32 weight percent; and copper in the range of 5–35 weight percent, preferably in the range of 10–30 weight percent, and most preferably in the range of 12–20 weight percent. The silver alloy can additionally contain zinc in the range of 0.1 to 2 weight percent, or other metals, such as palladium or indium, in a concentration less than 1 weight percent. Gold alloys can contain: gold in the range of 25–75 weight percent, preferably in the range of 45–70 weight percent, and most preferably in the range of 49–68 weight percent; silver in the range of 5–55 weight percent, preferably in the range of 10–50 weight percent, and most preferably in the range 15 to 40 weight percent; copper in the range of 5–25 weight percent, and preferably in the range of 7–22 weight percent; and palladium in the range of 0.5–12 weight percent, and preferably in the range of 0.1–9 weight percent. Other metals, such as zinc or indium, can have concentrations less than 2 weight percent. Metal oxides can, for example, be oxides of titanium, aluminum, zirconium, or calcium, and mixtures thereof, but are not limited to these examples. In addition, the filler can contain colloidal silica.

The overall weight percent of the filler particles, alone or in combination, can be in the range of 20–99.99 weight percent of the composition, preferably 30–99.9 weight percent, more preferably 40–99 weight percent. The particles used are preferably spherical in shape, although they may be filamentous or irregularly shaped. The average size range for the filler particles is preferably between 0.01 and 50 micrometers at the maximum diameter with a size range of 0.01 to 10 micrometers being preferable, although particles of metal oxides or colloidal silica having a dimension of approximately 0.01–0.04 micrometers can be used in the most preferred range.

Thin films of noble metals can be deposited on the surface of filler particles to permit the deposition of the thiol. The film should be of sufficient thickness such that treatment by an acid for a cleaning procedure will not dissolve the film.

The coupling agent can be a silane or a phosphate ester in the case thiol bonds cannot be formed on the surface of the metal. The silane has the formula $X-(CH_2)_n-Si-(OR)_3$, wherein R is a methyl or ethyl group, X is a group capable of reacting with components of the composition and n=1 to 3. The phosphate ester has the formula:

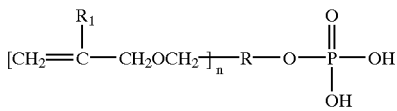

where:
R1 is a hydrogen atom, alkyl C1–C4, or CN, R is an aliphatic, cycloaliphatic or aryl radical containing from 1 to 10 carbon atoms and having a valence of n+1, n is an integer from 1 to 5, preferably from 3 to 5.

When not forming thiol bonds in solution, metal preparation for thiol deposition can take place in one or more phases, but is preferably divided into two phases. The first phase can use trichloroethylene, acetone, ethanol, or methanol, either alone or in any combination, to remove organic impurities from the surface. The second phase uses an acid to remove more strongly bound impurities.

Preferably, strongly bound impurities can be completely or almost completely removed by the acid exposure. Exposure to an acid, such as, but not limited to, nitric acid results in the formation of strong thiol bonds to the surface of the filler. Other acids include hydrochloric acid, sulfuric acid, hydrofluoric acid, maleic acid, phosphoric acid, oxalic acid, acetic acid, tetracetic acid, or fluoroboric acid.

Another method that can be used for preparing the surface of the filler for thiol deposition involves exposing the filler to concentrated sulfuric acid and 30% peroxide. The ratio of acid to peroxide can be 10 to 0.5, and preferably, 3 to 1.

Another method that can be used for thiol deposition on gold places the substrate in a 50/50 boiling solution of ethanol and chloroform.

Coupling agent agents such as γ-methacryloxypropyl trimethoxysilane (γ-MPS), 3-mercaptopropyl trimethoxysilane (MMPS), 2-mercaptoethyl methacrylate, or pentaerythritol triacrylate phosphoric acid ester can be used.

Thiol compounds can be of the form $HS-R^2-(Z)_n$, where $R^2$ represents an organic $C_1-C_{40}$ backbone, preferably $C_4-C_{32}$, and most preferably $C_6-C_{20}$. $R^2$ can contain aromatic, cyclic, ether, sulfide, acetal, amide, acetal, thioacetal or other non-polymerizing groups. One or more polymerizable groups, $(Z)_n$, where n=1 to 20, and preferably 1 to 12, are bonded to $R^2$. Each Z, chosen independently, contains an unsaturated group suitable for participation in free-radical polymerization. Z can be chosen to be a vinyl, an acryloxy, or a methacryloxy group but could also include various derivatives of acrylate, methacrylate, an allyl, a vinyl or a styrene or a derivative thereof. Depending on the moiety, the bond between Z and $R^2$ can be an ester, an amide, a urethane, an ether, or thioether, other linking bond appropriate to the purpose. The compound can be an organic disulfide of the formula $(Z)_n-R^2-S-S-R^2-(Z)_n$.

$R^2$ can be a straight-chain or branched alkane diradical. The polymerizable group or groups and the thiol can often be at opposing extremities of the $R^2$ group.

The thiol compound can be an omega terminated thioalkyl acrylate or diacrylate. Examples of omega terminated thioalkyl acrylates having a straight chain $R^2$ group are: 2-thioethyl acrylate, 3-thiopropyl acrylate, 4-thiobutyl acrylate, 6-thiohexyl acrylate, 10-thiodecyl acrylate.

Examples of omega terminated thioalkyl diacrylates having a branched chain $R^2$ group are:

1,2-diacryloyloxy-3-thiopropane ($HS-CH_2-CH(OCOCH=CH_2)-CH_2(OCOCH=CH_2)$), or 1,2-diacryloyloxy-6-thiohexane ($HS-(CH_2)_4-CH(OCOCH=CH_2)-CH_2(OCOCH=CH_2)$)

$R^2$ can contain aromatic groups, which can augment the hydrophobicity or ordering within the surface layer, or provide a means of branching, or substituted aromatic groups. Aromatic thiols can be 4-thiophenyl acrylate ($HS-C_6H_4-OCOCH=CH_2$), or 4-(6-thiohexyl) acrylate ($HS-(CH_2)_5-C_6H_4-OCOCH=CH_2$).

$R^2$ can be or contain a substituted ring compound, which can also be used to give a diacrylate. An example of a ring compound includes 2-thiobarbituryl diacrylate ($HS-C_4N_2H-(-OCOCH=CH_2)_2$), where the ring is aromatic.

$R^2$ may have other modifications, such as di(thio)acetal groups, in order to achieve a branched compound with multiple sites for polymerizable groups. Examples of this include 2-thioethyl bis(acrylolyoxyethyl) diacetal $HS-CH_2-CH_2-CH(-O-CH_2-CH_2-OCOCH=CH_2)_2$. The synthesis of this compound is described in U.S. Pat. No. 5,916,987.

For hardening in a tooth, the composition can be exposed to irradiation such as a laser light source, or a visible light source. The initiator system for laser or light curing includes agents which are sensitive to the wavelength of the light source. Agents sensitive for this purpose include, but are not limited to, camphorquinone, benzoin ethyl ether, and benzoin methyl ether. Tertiary amines can be used as reducing agents, and include but are not limited to such agents as N,N-dimethyl-p-toluidine, dimethylaminoethyl methacrylate, 4-(N,N-dimethylamino) benzoate, or dihydroxyethyl paratoluidine. The initiator system is present in the composition in an amount 0.05 to 5 percent by weight, preferably 0.1 to 3 percent by weight. For a two-paste system, the initiator is generally contained in one paste of the composition, and the accelerator, or reducing agent, is contained in another paste. The pastes contain the composition used for filling, or restoring a tooth, and include a polymerizable matrix material, fillers, coupling agents that couple the fillers to the matrix or other polymerizable components of the composition, and stabilizers. When ready to be placed in a tooth, the two pastes are mixed together, and the composition is applied to the tooth where it hardens. The pastes can be mixed by hand on a pad. The pastes can also be contained in a capsule having separate compartments, each compartment containing one of the pastes. The capsule is placed in a mixing device, such as one used for the mixing of the components of amalgam, and the two pastes are mixed together, and dispensed. The initiator and accelerator for this purpose include, but are not limited to, benzoyl peroxide, and N, N dimethyl-p-toluidine. The composition can also be hardened by microwave energy. Hardening by this method can be done outside the tooth, using a model of the tooth in which the filling is made. Hardening of the composition can be done directly in the tooth.

The composition can additionally contain polymerization inhibitors, such as hydroquinone, or 2,6-di-tertiary-butyl-para-cresol (butylated hydroxytoluene, BHT), and may contain pigments, such as iron oxides, to change the coloration of the composition.

The combination of materials used in this composition provides a material which has high strength characteristics, and is suitable for use as a filling material under load-bearing conditions.

The invention will be understood by reference to the following examples.

EXAMPLE 1

Measurement of Size Distribution of the Particles

The size and shape of silver-alloy particles (prepared by Special Metals, Ann Arbor, Mich.), which in this example, contain silver, tin, copper and palladium in the ratio of 49.5:30:20:0.5, are characterized by scanning electron microscopy (SEM) and image analysis software (SigmaScan Pro, Jandel Scientific, San Rafel, Calif.). Particle size distribution is determined by Sedigraph analysis. This method of analysis is based on Stoke's Law of fluid dynamics whereby particles are classified according to their rate of settling in a fluid, with sedimentation being dependent on the fluid viscosity and density. Particle size distribution is measured by an x-ray beam which passes through the fluid cell. X-ray intensity is measured and converted to percent of a given particle size.

The scanning electron micrograph (FIG. 1) generally confirms the near spherical nature of the particles while the image analysis indicates that the particle size ranged from approximately one to 12 mm in size. Roughly 85% of the particles were less than 10 mm, the preponderance being in the 4–7 mm range.

EXAMPLE 2

Coupling Agent Deposition

Figure 2:
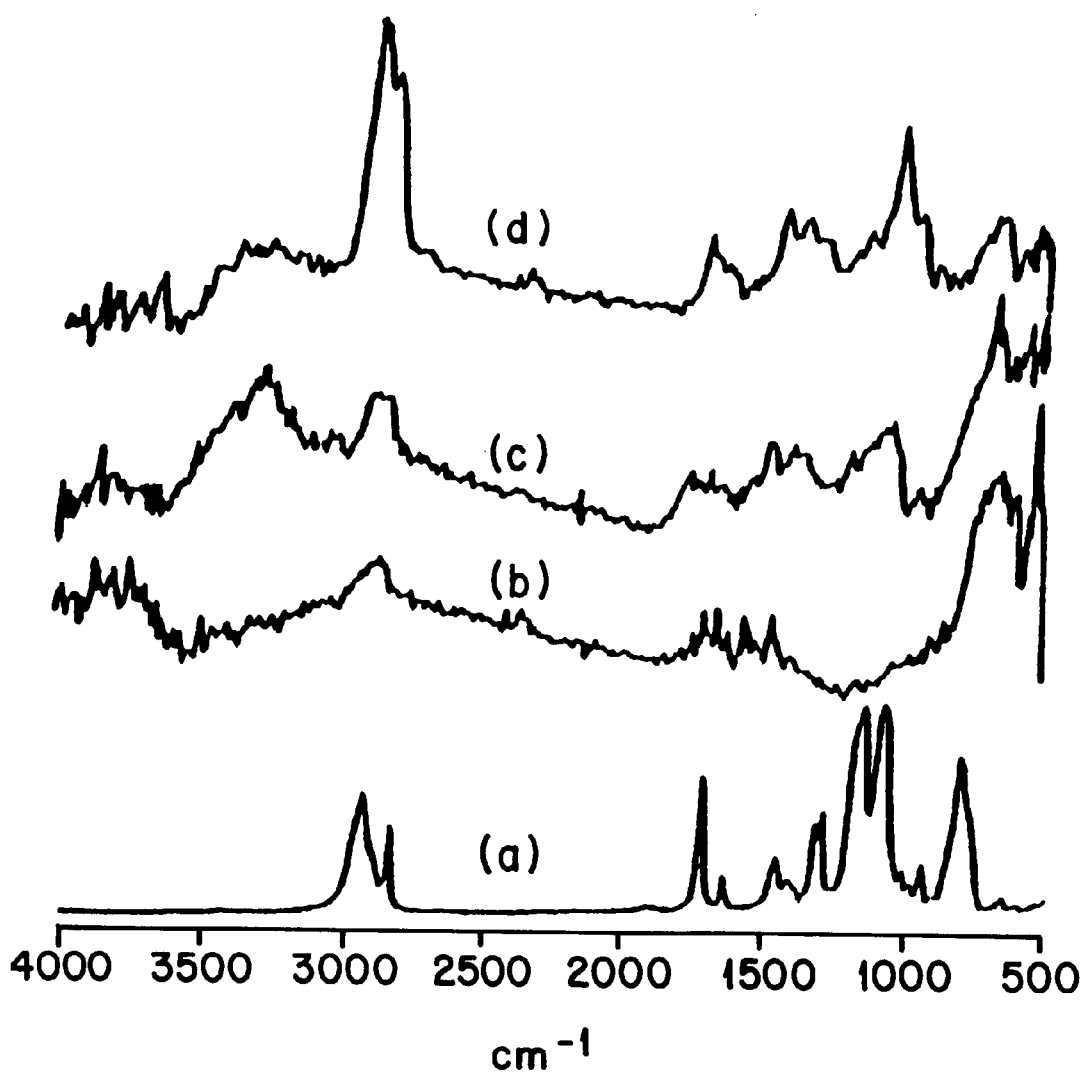
FIG. 2 is a spectral representation of PA-FTIR spectra of a γ-MPS solution, a silver alloy in an "as received" state, ethanol-washed alloy treated with γ-MPS, and ethanol and acid ($HBF_4$) treated silver as spectra (a), (b), (c) and (d) respectively.

The silver alloy is initially washed with ethanol (with ratio 1:10 by volume), and allowed to dry in a desiccator. To determine the ability to deposit a silane on the alloy, the particles were divided into two groups. The first consisted of the ethanol-washed particles, while the second was further treated with 10% fluoroboric acid ($HBF_4$) to remove surface contaminants. The acid-treated (e.g., cleaned) particles were rinsed with distilled water, then with a final wash of ethanol and allowed to air dry. Each of the powders was immersed in a 10% (by volume) solution of γ-MPS and ethanol in a clean plastic beaker. The volume of the solution was determined by calculating the γ-MPS to be 2 weight % of the alloy particle. The supernatant was then filtered off, and the residual powder was washed extensively with propanol. The propanol was again filtered, and the residual powder collected in a clean plastic beaker, which was placed in an oven at 110 degrees Celsius for eight hours. In order to evaluate the result of deposition, the photoacoustic Fourier transform infra-red (PA-FTIR) spectra were recorded of the γ-MPS solution, the silver alloy as received, the ethanol-washed alloy treated with γ-MPS, and the acid-cleaned alloy treated with γ-MPS. These spectra are respectively seen in FIG. 2 as (a), (b), (c) and (d).

Titanium dioxide ($TiO_2$) in an as-received state was similarly exposed to γ-MPS, dried in an oven and washed as previously described. Spectra were recorded of the $TiO_2$ before and after silanation. These spectra are respectively seen in FIG. 3(b) and (c). The spectrum of γ-MPS is shown as (a) for reference.

Figure 4:
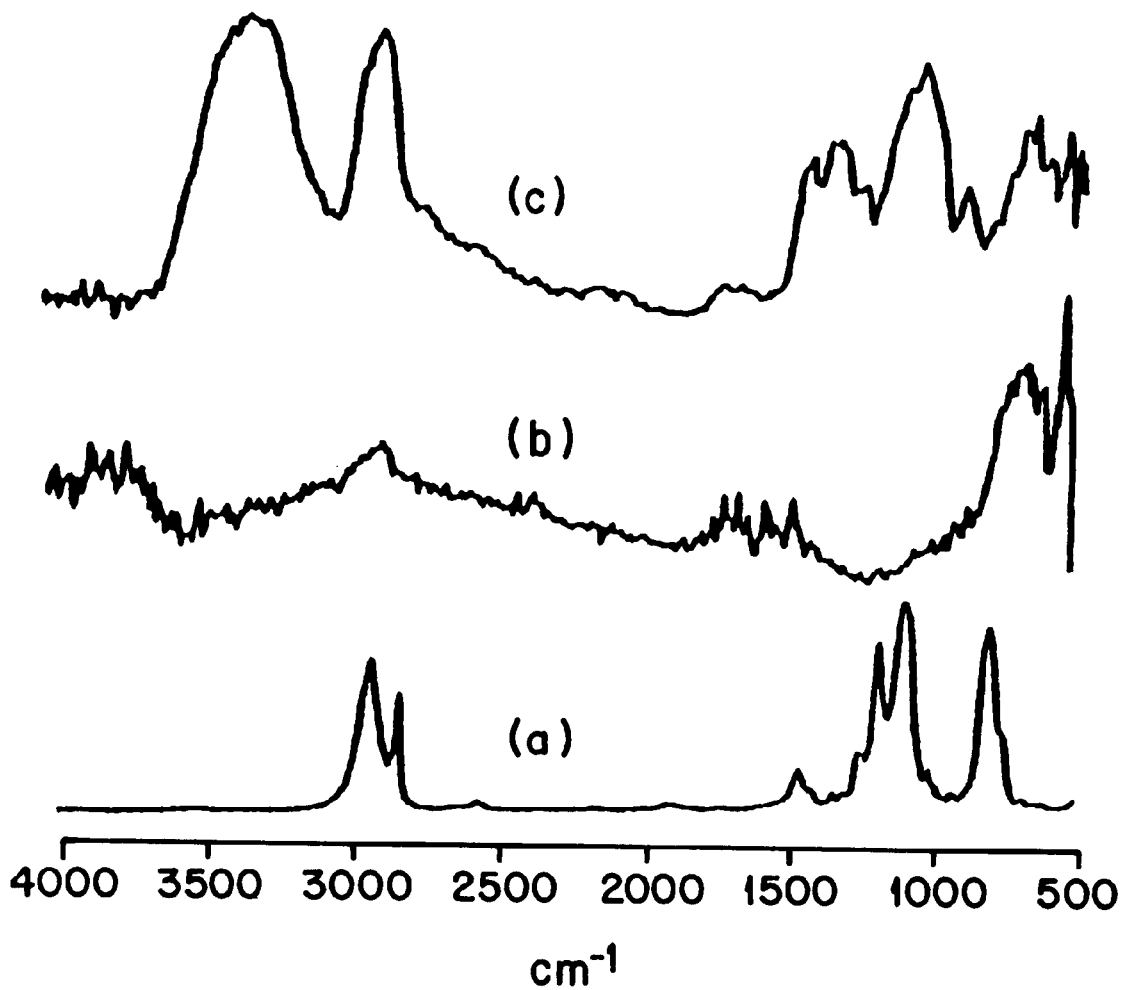
FIG. 4 is a spectral representation of a silver alloy, a 2% solution of 3-mercaptopropyl trimethoxysiliane (MMPS), and the silver alloy after treatment with MMPS as spectra (a), (b) and (c) respectively.

The process was repeated for the silver alloy using a thiol-containing silane in an attempt to determine if a sulfur-metal bond could be established. A 2% solution of 3-mercaptopropyl trimethoxysilane (MMPS) was made. Cleaned silver alloy was immersed in the solution, and processed in a fashion similar to the γ-MPS. Spectra of MMPS, the silver alloy, and the treated silver were recorded and are seen in FIG. 4 as (a), (b), and (c).

Figure 5:
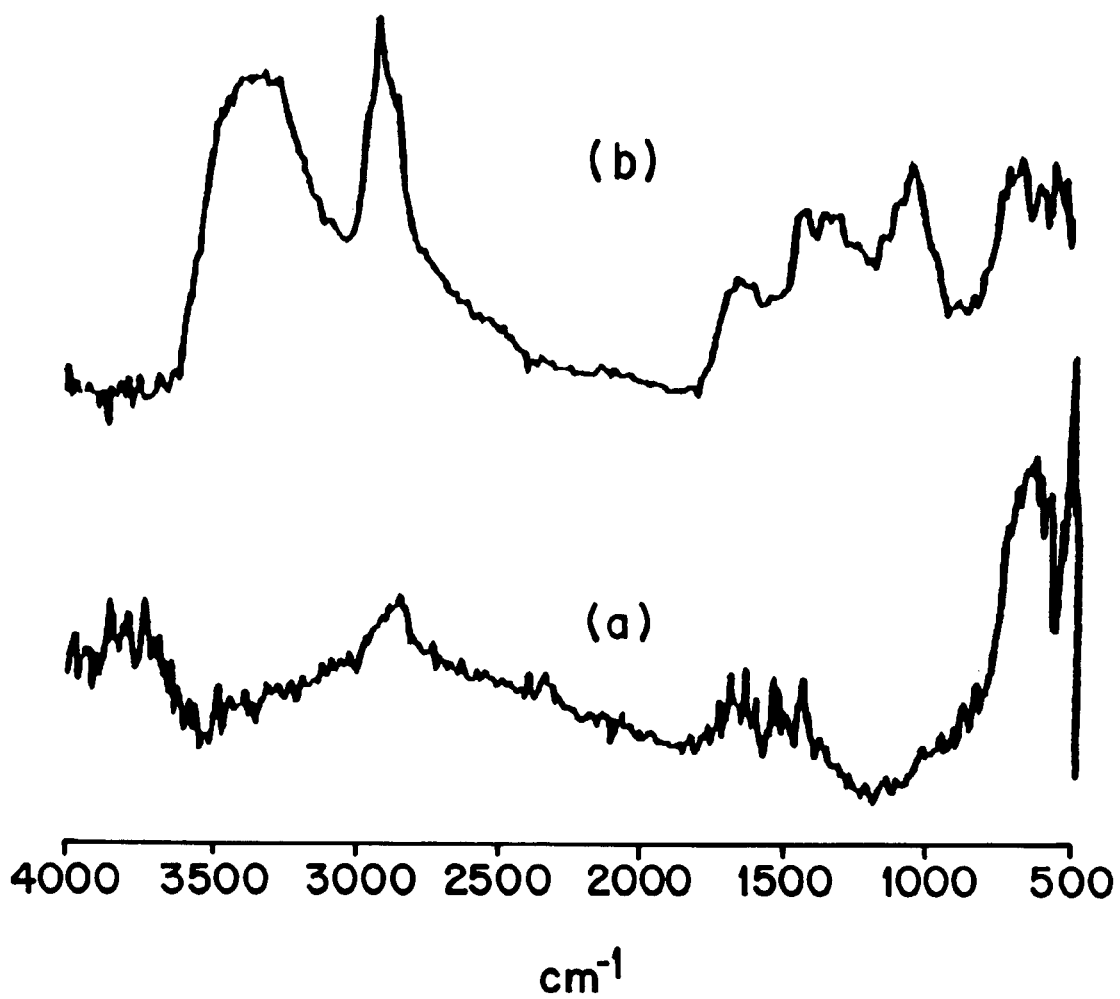
FIG. 5 is a spectral representation of the silver alloy, and cleaned (acid treated) silver alloy after treatment with an alkenethiol, shown respectively as spectra (a) and (b).

A thiol having the formula $HS-(CH_2)_{11}-CH_3$ was dissolved in ethanol so that the proportion of the thiol would be 6 weight % of the silver particles. Cleaned silver-tin-copper-palladium alloy particles were immersed in 20 mL of the thiol solution, which was then filtered off. The particles were recovered, washed four times with 100 mL of ethanol, and dried in a desiccator. Spectra of the powder before and after treatment were recorded, and are respectively shown as (a) and (b) in FIG. 5.

Figure 3:
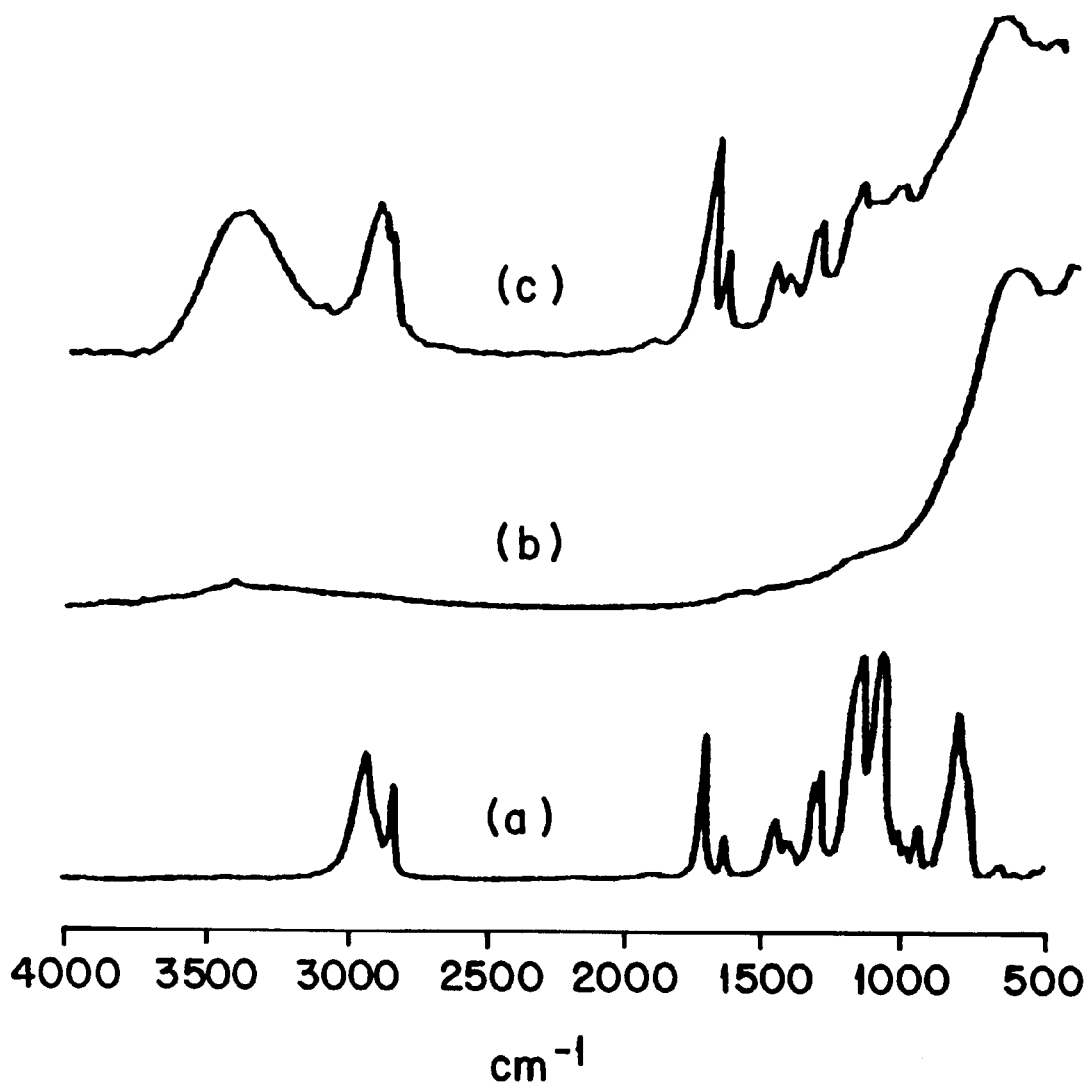
FIG. 3 is a spectral representation of γ-MPS solution, titanium dioxide ($TiO_2$) in an "as received" state, and titanium dioxide after exposure to γ-MPS as spectra (a), (b) and (c), respectively.

In FIGS. 2d, 3c and 4c, the absorption of either the γ-MPS or MMPS is demonstrated on both the silver alloy and titanium dioxide by the presence of strong bands attributed to the particular silane being used to treat the metal. Of equal importance, FIG. 2c indicates the relatively weak absorption of a silane when the metal is not cleaned, which emphasizes the importance of developing cleaning techniques for the successful deposition of adhesion promoters. The deposition of thiol on the silver alloy is further demonstrated in FIG. 5b, thus indicating that a thiol can, in fact, be deposited on a silver alloy. Adhesion promoters can be deposited on candidate metals to be used in the construction of a composite by this method.

EXAMPLE 2

Preparation of Thiolated Gold Colloid Capped with Methacrylate

One method of building up a thiol monolayer with chemical bonding at both ends is by subsequent chemical reactions on top of the solid substrate. A 2-step, layer-by-layer synthesis on gold was used.

Step 1—Preparation of Thiolated Gold Colloid:

In a 500 mL round-bottomed flask, 100 mL of $2 \times 10^{-3}$ M $AuCl_4$ (aq) was added to 300 mL of $1 \times 10^{-3}$ M ice-cold $NaBH_4$ (aq). The mixture was stirred for 10 minutes, 0.05 mL of $HS(CH_2)_2OH$ was added and stirring was continued for 6 hours. The precipitate was isolated by centrifuging. The product was washed with toluene and vacuum-dried.

Step 2—Esterification of Methacrylic Acid onto the Above OH-terminated Au Colloid:

The previous product of step 1, 0.05 mL of methacrylic acid, $CH_2CH(CH_3)COOH$, 0.1 mL DCC (dicyclohexylcarbodiimide), $(C_6H_{11}N)_2C$ and 6 mg of 4-dimethylamino pyridine (DMAP) were added to 10 mL of ether. The mixture was stirred overnight at room temperature. The supernatant liquid was decanted, leaving a gray solid which dried. The reaction byproducts were removed by washing with ethanol and centrifugation. Four rinses with 30 mL portions of ethanol were used to wash the product, after which the product was dried under vacuum. The FTIR spectrum showed intense C=O and C=C bonds (1716 and 1650 $cm^{-1}$), indicating the successful addition of chemically bonded, polymerizable vinyl groups to the metal particles.

EXAMPLE 3

Preparation of a Phosphate Ester

A solution of pentaerythritol triallyl ether (9.9 g) and triethylamine (3.8 g) in dry ether (60 ml) was slowly added into a solution of phosphorus oxychloride (15.3 g) in dry ether (60 ml) at 0 degrees with stirring. After addition of the solution, the mixture of two solutions was stirred for 16 hours at room temperature. The precipitation of the triethylamine hydrochloride was filtered off, and the solution was hydrolyzed by addition of the ether solution into ice water (100 ml) with stirring. The mixture was separated, and the ether layer was basified with sodium carbonate solution until pH=10, then acidified with hydrochloride acid until pH=4. The ether layer was extracted and dried by magnesium sulphate. The ether was extracted under reduced pressure to give pentaerythritol triacrylate, pentaerythritol triallyl ether as a clear colorless liquid. The $H^1$ NMR spectrum of this compound shows peaks around 6.2–5.8, 5.6–5.1, 4.5–4.1, 4.0–3.8, 3.6–3.4, 2.2–2.0 1.5–1.2, 1.0–0.8 ppm.

EXAMPLE 4

Effect of Thio-methacrylate Compound on Resin Adhesion to Silver

A pure silver rod having a diameter of 7 mm and length of approximately 30 mm was obtained from Aldrich (St. Louis, Mo.). The flat surface of the rod was abraded with aluminum oxide paper having 600 grit size. Composite resin was bonded under different conditions to the prepared surface after it was washed with 100 mL of ethanol. Six samples were prepared for each condition. Bonding surface conditions included nitric acid (concentrated nitric acid diluted by a factor of 3) treatment of the flat surface only, or nitric acid and a 6 percent solution of an allyl mercaptan in acetone. For both conditions, the nitric acid was washed off with 100 mL of deionized water, kept wet, and then washed with 100 mL of ethanol. The allyl mercaptan was applied to the surface of the nitric acid treated surface by a brush applicator. A composite resin, Bisfil II, shade B20, (Bisco, Schaumberg, Ill.) was placed into one half of a number 4 gelatin capsule. The capsule was positioned on the treated surface, and polymerized in place at each of four axes at 90 degrees to each other for 20 seconds using a visible light source. After application of allyl mercaptan, a thin overlayer of a mixture of Bis-GMA/TEGDMA at a ratio of 1:1 was placed. After 1 hour storage at room temperature, stress was applied at the interface between the metal-composite adhesive joint to the point of failure using a wire loop apparatus. The results are shown in the table that follows. The resin bonded by the allyl mercaptan showed a significant increase in strength compared to the group where no thiol-based adhesion promoter was used.

| Group | Mean Stress at Failure |
| --- | --- |
| Nitric acid only | 12.0 |
| Nitric acid and allyl mercaptan | 17.2 |
| | (values are in MPa) |

EXAMPLE 5

Effect of Thio-methacrylate Compound on Resin Adhesion to Silver

A pure silver rod having a diameter of 7 mm and length of approximately 30 mm was obtained from Aldrich (St. Louis, Mo.). The flat surface of the rod was polished sequentially by aluminum oxide paper having grit sizes of 600, 1200, and 200 abrasives, respectively. This was followed by applying a polishing suspension having 1 $\mu$m aluminum oxide particles (Buehler, Lake Bluff, Ill.). Composite resin was bonded under different conditions to the prepared surface after it was washed with 100 mL of ethanol. Six samples were prepared for each condition. Bonding surface conditions included (A) surface polish only, (B) group (A) treated with nitric acid, (C) group A primed with mercaptoethyl methacrylate (MEMA), (D) group (B) primed with MEMA. A composite resin, Bisfil II, shade B20, (Bisco, Schaumberg, Ill.) was placed into one half of a number 4 gelatin capsule. The capsule was positioned on the treated surface, and polymerized in place at each of four axis at 90 degrees to each other for 20 seconds using a visible light source. After application of MEMA, a thin overlayer of a mixture of Bis-GMA/TEGDMA at a ratio of 1:1 was placed. After 24 hours storage at room temperature, stress was applied at the interface between the metal-composite adhesive joint to the point of failure using a wire loop apparatus. Maximum stress was recorded at failure for the six specimens for each group, and mean stress (in MPa) at the point of failure of the adhesive joint was calculated. A fifth group (E) was subsequently evaluated for the effect of water storage. This group was the same as group (D), but stored in water at 37 degrees for 80 hours. The results are shown in the table that follows:

| Group | Mean Stress at Failure |
| --- | --- |
| (A) polished only, stored 24 h in air | 9.3 |
| (B) polished, $HNO_3$, stored 24 h in air | 12.0 |
| (C) polished, MEMA, stored 24 h in air | 7.4 |
| (D) polished, $HNO_3$, MEMA, stored 24 h in air | 25.7 |
| (E) polished, $HNO_3$, MEMA, stored 80 h in water | 27.1 |
| | (values are in MPa) |

These data show that combination of acid treatment and the use of an omega terminated thiol compound provides high strength bonds between a metal and a polymerizable resin. Furthermore, the bonds formed are stable in water.

EXAMPLE 6

Effect of Metal Reinforcement

Standard bars (n=4) measuring 25×2×2 mm were made of a 50:50 Bis-GMA/TEGDMA mixture, and the same mixture (n=5) filled with silanated silver alloy particles and titanium dioxide in a weight ratio of 4:1. The filler volume was 70 %. Using the two paste method described in the specifications, the composite was chemically hardened by a peroxide/amine system. After 24 hours, the bars were submitted to a three-point bend test in an Instron electromechanical testing instrument. Flexural strength was calculated from failure loads, and mean values and (standard deviations) were respectively 17.8 (4.2) and 36.3 (8.7) MPa. The dental polymers are reinforced by modified metal particulates.

EXAMPLE 7

Synthesis of Bifunctional Alkylthiols

There are three possible synthetic approaches in developing bifunctional thiol compounds. The first involves the synthesis of an $\omega$-thioethyl methacrylate by esterification of 2-thioethanol with methacryl chloride. A second method uses the disulfide form of the thiol compounds throughout the synthesis, while a third method involves a solid state synthesis where the metal particles are first coated with $\omega$-thio alcohol, and then reacted with methacryl chloride to add the methacryl group to the thiol. The latter two are described in more detail.

An $\omega$-thioethyl methacrylate synthesized from a mixture of 2-mercaptoethanol and methacryl chloride. Normally, thiols were applied using dilute (<$10^{-3}$ M) ethanol solutions to achieve full, well-ordered monolayer coverages. Generally, little difference was observed if the dilute thiol solution is replaced with a disulfide form. Here, a bis-(w-ethyl methacrylate) disulfide compound was prepared in the presence of tetrahydrofluoran to form an omega terminated thiol compound according to the following reaction:

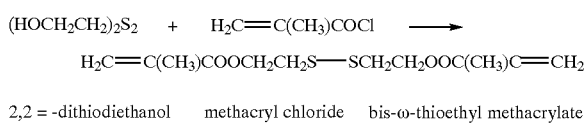

2,2 = -dithiodiethanol  methacryl chloride  bis-ω-thioethyl methacrylate

Another synthetic method involved protecting the thiol group during the reaction of the alcohol with the methacryl chloride, this time by adsorbing the ω-thio alcohol onto a solid substrate. Adsorption takes place exclusively at the thiol group, leaving the outer surface of the particle rich in hydroxyl groups. The reaction proceeded as follows: $AuCl_4$ was added to $NaBH_4$ in water. 2-thioethanol was then added to cap the particles of colloidal gold and stop the reaction. After extensive washing with water, the colloid was separated by centrifugation. The silver was then re-suspended in water, and the outer —OH groups were reacted with excess methacryl chloride. Again, the particles were extensively washed and centrifuged for collection.

EXAMPLE 8

Compounds, such as dithioerythritol dimethacrylate, can be prepared by the following scheme:

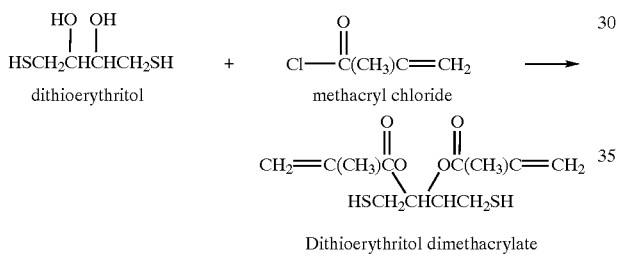

In a first step, the —SH group is protected by reaction of the —SH group of dithioerythritol with methoxymethyl isocyanate (MI) as follows:

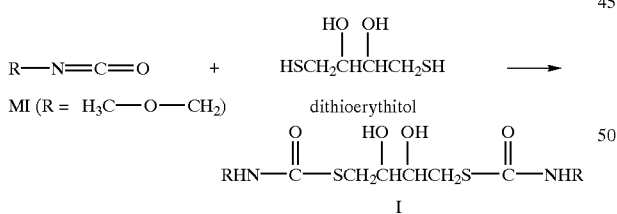

MI is well-suited for rapid and selective carbamoylation of the —SH group at pH 4–5 in an aqueous medium and at room temperature.

In a second step, product (I) is esterified with methacryl chloride as follows:

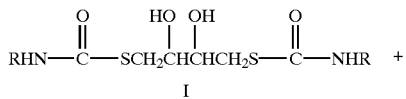

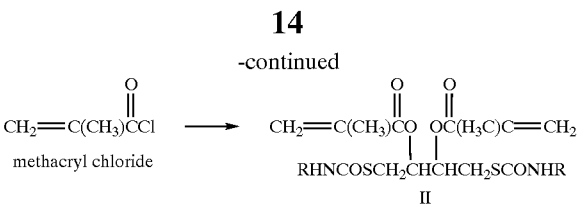

In a third step, the —SH protecting groups are removed by the addition of glycylglycine, which traps methoxymethyl isocyanate, at room temperature. This removal procedure is carried out under nitrogen to avoid undesired re-oxidization of the —SH groups.

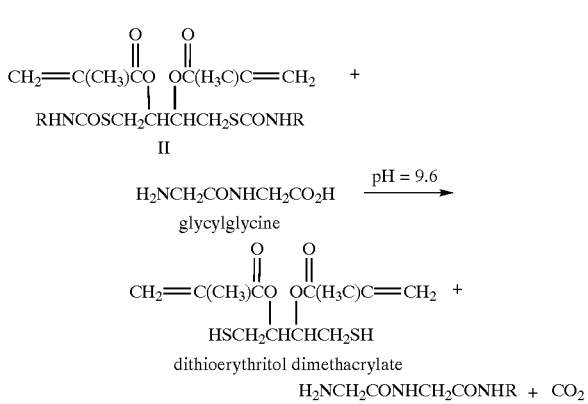

EXAMPLE 9

Additional coupling agents can be prepared by esterification from disulphides. In a first synthetic step, thiols are oxidized to disulphides, for example, with iodine. A solution of iodine ($I_2$) is added to the solution of dithioerythritol with vigorous stirring. The product (II) is produced as follows:

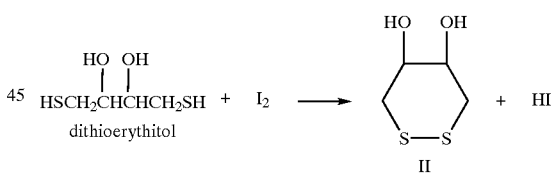

The oxidization can also occur electrochemically in methanolic solution at a silver or platinum electrode by the following reaction:

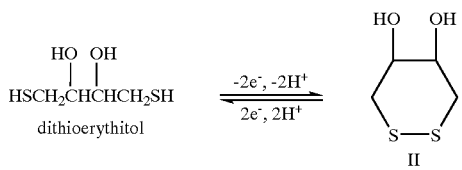

Disulfides having different structures are synthesized. A compound such as 3-mercapto-1,2-propanediol, which can be purchased (Aldrich Inc., Milwaukee, Wis.), is oxidized to form a disulfide as follows:

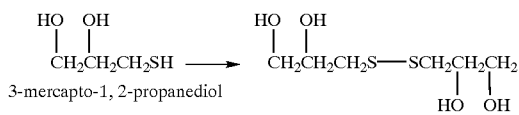

The disulfide is esterified, for example, by the following reactions:

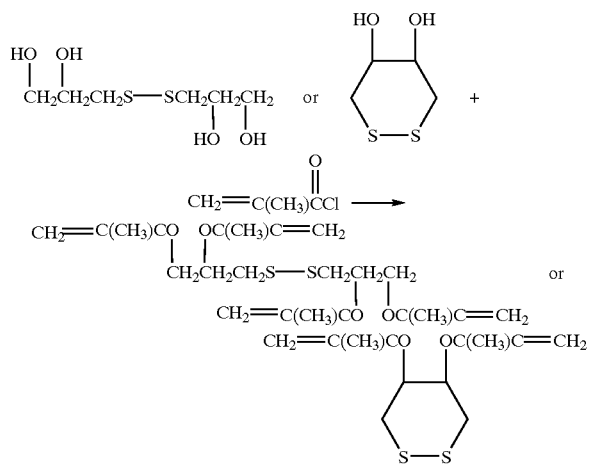

EXAMPLE 10

The conversion of alcohol hydroxyls to a thiol is achieved though the well-known thiourea alkylation procedure for the synthesis of thiols. In this reaction, the OH group of glycerol dimethacrylate first reacts with SCl group of p-toluenesulfonyl chloride to form a strong polar group of —$OSO_2$—. This reaction generally occurs at 0° C. and ambient atmosphere, and is shown as:

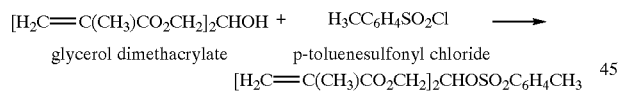

The —$OSO_2$— group of the above product is replaced by thiourea to form the isothiouronium salt in the reaction shown below. An inhibitor, such as 2,2'-methylene bis(4-ethyl-6-tert-butylphenol), is added to the thiourea solution to prevent the polymerization of the glycerol dimethacrylate.

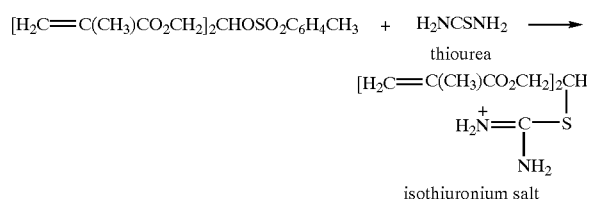

The isothiouronium salt is dissolved by hydrochloric acid to form the final product, glycerothiol dimethacrylate.

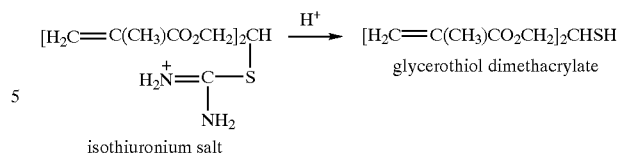

EXAMPLE 11

Micron-sized silver-tin alloy particles having been surface-modified with a thin film of gold or silver are placed in an ethanol solution. Dithioerythritol is then added to cap the particles. The alloy is washed by water and separated by centrifugation, leaving a monolayer on the surface. The alloy covered with dithiothreitol is added to a solution of methacryl chloride to produce alkenethiols on the surface of metal or alloy. The particles covered with alkenethiols is washed again to remove excess methacryl chloride, and used to construct composite. The reaction is shown schematically below:

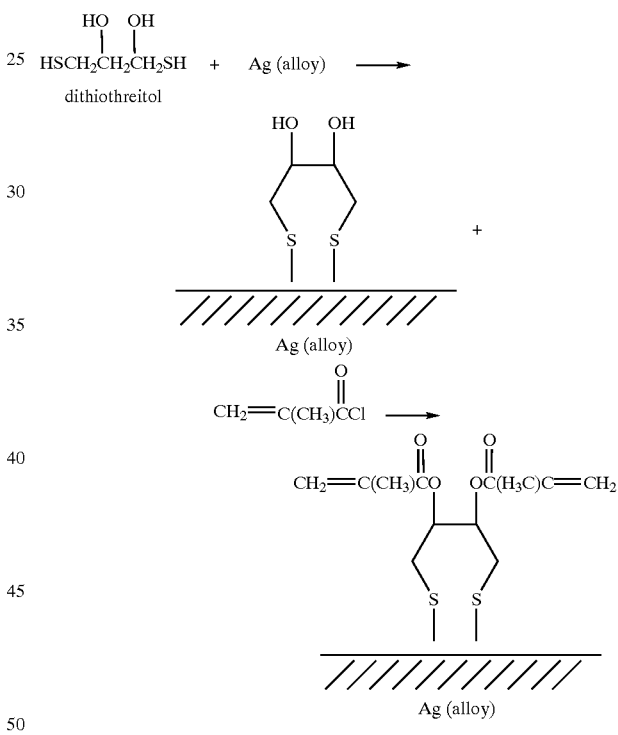

While this invention has been described in connection with specific embodiments, it should be understood that is it capable of further modification. The claims herein are intended to cover those variations which one skilled in the art would recognize as the chemical equivalent of what has been described herein. Thus, various omissions, modifications, and changes to the principles described herein may be made by one skilled in the art without departing from the true scope of the invention which is indicated by the following claims.

What is claimed is:

1. A composition comprising a polymerizable material in an amount of from about 1 to about 79 pecent by weight of the composition, filler particles in an amount of from about 20 to about 98 percent by weight of the composition, said filler particles having a metal surface that is capable of

17 forming a bond with at least one of a thiol or a phosphate, wherein the metal is selected from groups VIIB, VIII, IB, and IVA of the periodic table of the elements or their oxides; and a coupling agent including a functionality capable of forming a bond with the metal, and said coupling agent comprising at least one of a thiol-containing compound or a polymerizable phosphate.

2. The composition of claim 1, wherein the filler is selected from the group consisting of a metal particulate, a metal alloy particulate, a metal oxide particulate, and combinations thereof.

3. The composition of claim 1, wherein the polymerizable material includes an acrylate monomer, a methacrylate monomer, a phosphate of an acrylate monomer, or a phosphate of a methacrylate monomer.

4. The composition of claim 1, wherein the polymerizable material includes a monomer selected from the group consisting of 2,2-bis(4-2-hydroxy-3-methacrylyloxypropoxy)phenyl)propane, ethyleneglycol dimethacrylate, triethyleneglycol dimethacrylate, 1,6-hexamethylene glycol dimethacrylate (HGDMA), trimethylolpropane trimethacrylate, urethane dimethyacrylate, 2-hydroxyethyl methacrylate, 2-hydroxy methylmethacrylate, pentaerythritol triacrylate, and pentaerythritol tetraacrylate.

5. The composition of claim 1, wherein the polymerizable material includes pentaerythritol triallyl ester monophosphate or ethyl methacrylate monophosphate.

6. The composition of claim 1, wherein the filler is a particulate measuring from 0.02 to 50 microns.

7. The composition of claim 1, wherein the filler includes silver, gold, silver alloy, or gold alloy.

8. The composition of claim 1, wherein the filler includes a metal oxide.

9. The composition of claim 1, wherein the coupling agent has the formula:

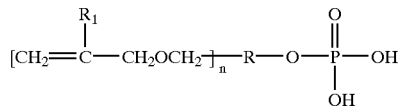

where:

R1 is a hydrogen atom, alkyl C1–C4, or CN,

R is an aliphatic, cycloaliphatic or aryl radical containing from 1 to 10 carbon atoms and having a valence of n+1, and n is an integer from 1 to 5.

10. A composite comprising a filler having a coating of a metal and an omega-terminated thiol or disulfide having the formulae:

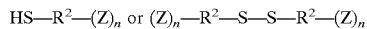

where HS is the thiol, $R^2$ is the linkage between the thiol and omega termination being comprised of $(CH_2)_m$, m is an integer from 2 to 20, n is an integer from 1 to 20, and Z is the reactive omega termination having at least one unsaturated group.

18

11. The composite of claim 10, wherein m is 6 to 12.

12. The composite of claim 10, wherein Z is a vinyl, an acryloxy, or a methacryloxy group.

13. The composite of claim 10, wherein filler has a coating including gold or silver.

14. The composition of claim 1, wherein the filler is a metal oxide selected from the group consisting of colloidal silica, titanium dioxide, iron oxide, zirconia, and mixtures thereof.

15. The composition of claim 1, wherein the polymerizable material is a spiro orthocarbonate.

16. A composition comprising a polymerizable material in an amount of from about 1 to about 79 percent by weight of the composition, filler particles present in mount of a from about 20 to 98 percent by weight, said filler particles having a surface which is capable of forming a bond with sulphur, and a thiol coupling agent in an effective amount.

17. A method of preparing a composite comprising:

coupling a surface of a filler having a coating of a metal to a coupling agent having the formulae:

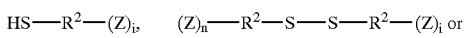

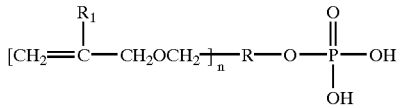

where HS is the thiol, $R^2$ is the linkage between the thiol and omega termination being comprised of $(CH_2)_m$, m is an integer from 2 to 20, i is an integer from 1 to 20, Z is the reactive omega termination having at least one unsaturated group, R1 is a hydrogen atom, alkyl C1–C4, or CN, R is an aliphatic, cycloaliphatic or aryl radical containing from 1 to 10 carbon atoms and having a valence of n+1, and n is an integer from 1 to 5.

18. The composition of claim 1, wherein said coupling agent comprises said thiol-containing compound.

19. A method of filling a tooth comprising applying a composition to a surface of a tooth, the composition including a polymerizable material in an amount of from about 1 to about 79 percent by weight of the composition, filler particles in an amount of from about 20 to about 98 percent by weight of the composition, said filler particles having a metal surface that is capable of forming a bond with at least one of a thiol or a phosphate ester, wherein said metal is selected from groups VIIB, VIII, IB, IIB, and IVA of the periodic table of the elements or their oxides; and a coupling agent including a functionality capable of forming a bond with the surface, said coupling agent being provided on said filler particles, and the coupling agent comprising at least one of a thiol-containing compound or a polymerizable phosphate; and curing the composition.

* * * * *